United States Patent [19]

Moore

[11] Patent Number: 5,180,587
[45] Date of Patent: Jan. 19, 1993

[54] TABLET FORMULATIONS OF PESTICIDES

[75] Inventor: Earl P. Moore, Anderson, S.C.

[73] Assignee: E. I. Du Pont de Nemours and Company, Wilmington, Del.

[21] Appl. No.: 613,836

[22] PCT Filed: May 17, 1989

[86] PCT No.: PCT/US89/02072
§ 371 Date: Dec. 6, 1990
§ 102(e) Date: Dec. 6, 1990

Related U.S. Application Data

[63] Continuation-in-part of Ser. No. 212,668, Jun. 28, 1988, abandoned.

[51] Int. Cl.⁵ .................. A01N 25/12; A61K 9/46
[52] U.S. Cl. .................... 424/408; 424/405; 424/465; 424/466; 424/717

[58] Field of Search ............... 424/403, 405, 408, 465, 424/466, 717

[56] References Cited

U.S. PATENT DOCUMENTS

| | | | |
|---|---|---|---|
| 3,518,343 | 6/1970 | Welsh et al. | 424/717 |
| 4,111,202 | 9/1978 | Theeuwes | 128/260 |
| 4,564,363 | 1/1986 | Bagnall et al. | 604/891 |
| 4,888,177 | 12/1989 | Gergely et al. | 424/466 |
| 4,994,273 | 2/1991 | Zentner et al. | 424/422 |

Primary Examiner—Thurman K. Page
Assistant Examiner—Neil Levy
Attorney, Agent, or Firm—James A. Costello

[57] ABSTRACT

A tablet formulation comprising: (i) a pesticide characterized by low or no water solubility, and (ii) a complementary delivery system containing an organic acid, an inorganic base, a dispersant, a disintegrant, and a wetting agent.

20 Claims, No Drawings

TABLET FORMULATIONS OF PESTICIDES

CROSS-REFERENCE TO RELATED APPLICATION

This is a continuation-in-part via the PCT of U.S. application Ser. No. 212,668, filed on Jun. 28, 1988, now abandoned.

BACKGROUND OF THE INVENTION

This invention concerns specific pesticide formulations especially suited for commercial use in tablet form. Several types of tablet formulations are known in the art. See, for instance, G. B. 2,139,893; G. B. 2,184,946; U.S. Pat. No. 4,182,620 and Kokai 51088641. However, these publications do not disclose or suggest the specific combinations of active ingredient(s) and delivery system(s) of this invention. The formulations of this invention afford rapid disintegration and dispersion, even in cold water, of pesticidally active compounds that are water insoluble or of very low water solubility.

SUMMARY OF THE INVENTION

This invention concerns a tablet formulation consisting essentially of, by total weight of the formulated composition:

(i) about 20% to 75% of a pesticide characterized by a melting point of at least about 100° C. and solubility in neutral water at 20° C. of no more than about 5% by weight, and (ii) about 25% to 80% of a delivery system characterized by a panel of components complementary to the pesticide of (i).

Typically, the delivery system (ii) will contain the following components in these amounts by weight of the total composition:

(a) about 5% to 20% of a dibasic or tribasic organic carboxylic acid or a mixture thereof;
(b) about 7% to 50% of an ammonium or alkali metal carbonate or bicarbonate or a mixture thereof;
(c) about 0.5% to 20% of a dispersant;
(d) about 0.1% to 5% of water-insoluble cross-linked polyvinylpyrrolidone; and
(e) about 0.1% to 5% of an anionic or nonionic wetting agent.

The delivery system is characterized by the interrelationship of components (a) to (e) in the recited ranges to effect rapid disintegration of finely dispersed pesticide particles (i).

By "tablet formulation" is meant the tablet made from the composition described herein, as well as the composition formulated in accordance with this disclosure but not in tablet form.

Contemplated pesticides include those selected from the following classes, including mixtures thereof: herbicides, fungicides, bactericides, insecticides, nematocides, acaricides, and growth regulants.

Preferred dibasic and tribasic organic carboxylic acids include citric, fumaric, phthalic, maleic, malic, oxalic, adipic, glutaric, 2-methyl glutaric, succinic and tartaric, or mixtures of any of them. Preferred carbonates and bicarbonates include the lithium, sodium, and potassium salts or mixtures of any of them.

The term "dispersants" includes sodium salts of naphthalene formaldehyde condensates; sodium, potassium and calcium salts of naphthalene sulfonic acid condensates; lithium, sodium, potassium, calcium, and ammonium salts of lignosulfonates such as Polyfon H ® and Lignosol TSF ®; sodium, potassium and ammonium salts of polyacrylates and carboxylates, e.g., Tamol 731 SD; sodium salts of maleic anhydride-isobutylene copolymers; and water soluble nonionic polymers such as polyvinylpyrrolidone, polyethylene oxides and cellulose derivatives. Preferred dispersants include the sodium, potassium, ammonium and calcium salts of naphthalene sulfonic acid condensates, with the ammonium salts, specifically Lomar PWA, more preferred.

Water-insoluble, cross-linked polyvinylpyrrolidone disintegrant refers to any of the generic crospovidone disintegrating agents. Specifically preferred is Polyplasdone ® XL 10.

The term "anionic wetting agent" includes alkylbenzene sulfonates, alkyl and dialkylnaphthalene sulfonates, alkyl and alcohol sulfates, sulfoalkylamides, carboxylates, alpha-olefin sulfonates and dialkyl sulfosuccinates. The term "nonionic wetting agent" includes acetylenic diols, ethylene oxidepropylene oxide copolymers, alkylphenol ethoxylates, fatty acid ethoxylates, alcohol ethoxylates, sorbitan fatty acid ester ethoxylates and castor oil ethoxylates. The preferred wetting agents are sodium dialkyl sulfosuccinates of which sodium diisobutyl sulfosuccinate (Monawet MB-100), sodium diamyl sulfosuccinate and sodium dicyclohexyl sulfosuccinate are more preferred.

DETAILS OF THE INVENTION

Preferred pesticides are those listed in Table 1.

TABLE 1

| Cmpd. No. | Common Name | m.p. (°C.) | Chemical Name |
|---|---|---|---|
| | | HERBICIDES | |
| 1 | acifluorfen | 142–160 | 5-[2-(chloro-4-(trifluoro methyl)phenoxy]-2-nitro-benzoic acid |
| 2 | asulam | 142–144 | methyl [(4-aminophenyl)-sulfonyl]carbamate |
| 3 | atrazine | 175–177 | 6-chloro-N-ethyl-N'-(1-methylethyl)-1,3,5-triazine-2,4-diamine |
| 4 | bensulfuron methyl | 185–188 | 2-[[[[(4,6-dimethoxy-2-pyrimidinyl)amino]-carbonyl]amino]sulfonyl]-methylbenzoic acid, methyl ester |
| 5 | bentazon | 137–139 | 3-(1-methylethyl)-1H-2,1,3-benzothiadiazin-4(3H)-one, 2,2-dioxide |
| 6 | bromacil | 158–159 | 5-bromo-6-methyl-3-(1-methyl- |

TABLE 1-continued

| Cmpd. No. | Common Name | m.p. (°C.) | Chemical Name |
|---|---|---|---|
| | | | propyl)-2,4(1H,3H)pyrimidinedione |
| 7 | bromoxynil | 194–195 | 3,5-dibromo-4-hydroxybenzonitrile |
| 8 | chloramben | 200–201 | 3-amino-2,5-dichlorobenzoic acid |
| 9 | chlorimuron ethyl | >100 | 2-[[[[(4-chloro-6-methoxy-2-pyrimidinyl)amino]carbonyl]amino]sulfonyl]benzoic acid, ether ester |
| 10 | chloroxuron | 151–152 | N'-[4-(4-chlorophenoxy)-phenyl]N,N-dimethylurea |
| 11 | chlorsulfuron | 174–178 | 2-chloro-N-[[(4-methoxy-6-methyl-1,3,5-triazin-2-yl)-amino]carbonyl]benzenesulfonamide |
| 12 | chlortoluron | 147–148 | N'-(3-chloro-4-methylphenyl)-N,N-dimethylurea |
| 13 | clomazone | 151–152 | 2-[(2-chlorophenyl)methyl]-4,4-dimethyl-3-isoxazolidinone |
| 14 | cyanazine | 166–167 | 2-[[4-chloro-6-(ethylamino)-1,3,5-triazin-2-yl]amino]-2-methylpropanenitrile |
| 15 | dazomet | 104–105 | tetrahydro-3,5-dimethyl-2H-1,3,5-thiadiazine-2-thione |
| 16 | desmediphan | 120 | ethyl [3-[[(phenylamino)-carbonyl]oxy]phenyl]-carbamate |
| 17 | dicamba | 114–116 | 3,6-dichloro-2-methoxybenzoic acid |
| 18 | dichlobenil | 139–145 | 2,6-dichlorobenzonitrile |
| 19 | dichlorprop | 117–118 | (±)-2-(2,4-dichlorophenoxy)-propanoic acid |
| 20 | diphenamid | 134–135 | N,N-dimethyl-α-phenylbenzeneacetamide |
| 21 | dipropetryn | 104–106 | 6(ethylthio)-N,N'-bis(1-methylethyl)-1,3,5-triazine-2,4-diamine |
| 22 | diuron | 158–159 | N'-(3,4-dichlorophenyl)-N,N-dimethylurea |
| 23 | thiameturon | >100 | 3-[[[[(4-methoxy-6-methyl-1,3,5-triazin-2-yl)amino]-carbonyl]amino]sulfonyl]-2-thiophenecarboxylic acid, methyl ester |
| 24 | — | >100 | 2-[[[[N-(4-methoxy-6-methyl-1,3,5-triazine-2-yl)-N-methylamino]carbonyl]-amino]sulfonyl]benzoic acid, methyl ester |
| 25 | fenac | 156 | 2,3,6-trichlorobenzeneacetic acid |
| 26 | fenuron | 133–134 | N,N-dimethyl-N'-phenylurea |
| 27 | fluometuron | 163–164 | N,N-dimethyl-N'-[3-(trifluoromethyl)phenyl]urea |
| 28 | fluridone | 151–154 | 1-methyl-3-phenyl-5-[3-(trifluoromethyl)phenyl]-4(1H)-pyridinone |
| 29 | fomesafen | 220–221 | 5-[2-(chloro-4-(trifluoromethyl)phenoxy]-N-(methylsulfonyl)-2-nitrobenzamide |
| 30 | glyphosate | 200 | N-(phosphonomethyl)glycine |
| 31 | hexazinone | 115–117 | 3-cyclohexyl-6-(dimethylamino)-1-methyl-1,3,5-triazine-2,4(1H,3H)-dione |
| 32 | imazamethabenz | >100 | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| 33 | imazaquin | 219–222 | 2-[4,5-dihydro-4-methyl-4-(1-methylethyl)-5-oxo-1H-imidazol-2-yl]-3-quinolinecarboxylic acid |
| 34 | imazethapyr | 172–175 | (±)-2-(4,5-dihydro-4-methyl-4-(1-methylethyl)-5-oxo-1H-imidazol-2-yl]-5-ethyl-3-pyridinecarboxylic acid |
| 35 | ioxynil | 209 | 4-hydroxy-3,5-diiodobenzo- |

TABLE 1-continued

| Cmpd. No. | Common Name | m.p. (°C.) | Chemical Name |
|---|---|---|---|
| | | | nitrile |
| 36 | isoproturon | 155–156 | N-(4-isopropylphenyl)-N',N'-dimethylurea |
| 37 | isouron | 119–120 | N'-[5-(1,1-dimethylethyl)-3-isoxazolyl]-N,N-dimethylurea |
| 38 | isoxaben | 176–179 | N-[3-(1-ethyl-1-methylpropyl)-5-isoxazolyl]-2,6-dimethoxybenzamide |
| 39 | karbutilate | 176–178 | 3-[[(dimethylamino)carbonyl]-amino]phenyl-(1,1-dimethylethyl)carbamate |
| 40 | lenacil | 316–317 | 3-cyclohexyl-6,7-dihydro-1H-cyclopentapyrimidine-2,4-(3H,5H)dione |
| 41 | MCPA | 100–115 | (4-chloro-2-methylphenoxy)-acetic acid |
| 42 | MCPB | 100 | 4-(4-chloro-2-methylphenoxy)-butanoic acid |
| 43 | mefluidide | 183–185 | N-[2,4-dimethyl-5-[[(trifluoromethyl)sulfonyl]-amino]phenyl]acetamide |
| 44 | methabenzthiazuron | 119–120 | 1,3-dimethyl-3-(2-benzothiazolyl)urea |
| 45 | methazole | 123–124 | 2-(3,4-dichlorophenyl)-4-methyl-1,2,4-oxadiazolidine-3,5-dione |
| 46 | metribuzin | 125–126 | 4-amino-6-(1,1-dimethylethyl)-3-(methylthio)-1,2,4-triazin-5(4H)-one |
| 47 | metsulfuron methyl | 163–166 | 2-[[[[(4-methoxy-6-methyl-1,3,5-triazin-2-yl)amino]-carbonyl]amino]sulfonyl]-benzoic acid, methyl ester |
| 48 | monuron | 174–175 | N'-(4-chlorophenyl)-N,N-dimethylurea |
| 49 | naptalam | 185 | 2-[(1-naphthalenylamino)-carbonyl]benzoic acid |
| 50 | neburon | 102–103 | 1-butyl-3-(3,4-dichlorophenyl)-1-methylurea |
| 51 | nitralin | 151–152 | 4-(methylsulfonyl)-2,6-dinitro-N,N-dipropylaniline |
| 52 | norflurazon | 174–180 | 4-chloro-5-(methylamino)-2-[3-(trifluoromethyl)phenyl]-3(2H)-pyridazinone |
| 53 | oryzalin | 141–142 | 4-(dipropylamino)-3,5-dinitrobenzenesulfonamide |
| 54 | perfluidone | 142–144 | 1,1,1-trifluoro-N-[2-methyl-4-(phenylsulfonyl)phenyl]-methanesulfonamide |
| 55 | phenmedipham | 143–144 | 3-[(methoxycarbonyl)amino]-phenyl (3-methylphenyl)-carbamate |
| 56 | picloram | >215 (DEC) | 4-amino-3,5,6-trichloro-2-pyridinecarboxylic acid |
| 57 | prometryn | 118–120 | N,N'-bis(1-methylethyl)-6-(methylthio)-1,3,5-triazine-2,4-diamine |
| 58 | pronamide | 155–156 | 3,5-dichloro-N-(1,1-dimethyl-2-propynyl)benzamide |
| 59 | propazine | 212–214 | 6-chloro-N,N'-bis(1-methylethyl)-1,3,5-triazine-2,4-diamine |
| 60 | pyrazon | 205–206 | 5-amino-4-chloro-2-phenyl-3(2H)pyridazinone |
| 61 | siduron | 133–138 | N-(2-methylcyclohexyl)-N'-phenylurea |
| 62 | simazine | 225–227 | 6-chloro-N,N'-diethyl-1,3,5-triazine-2,4-diamine |
| 63 | sulfometuron methyl | 182–189 | 2-[[[[(4,6-dimethyl-2-pyrimidinyl)amino]carbonyl]-amino]sulfonyl]benzoic acid, methyl ester |
| 64 | tebuthiuron | 161–164 | N-[5-(1,1-dimethylethyl)-1,3,4-thiadiazol-2-yl]-N,N'-dimethylurea |
| 65 | terbacil | 175–177 | 5-chloro-3-(1,1-dimethylethyl)-6-methyl-2,4(1H,3H)-pyrimidinedione |
| 66 | terbuthylazine | 177–179 | 2-(tert-butylamino)-4-chloro-6-(ethyl-amino)-s-triazine |

TABLE 1-continued

| Cmpd. No. | Common Name | m.p. (°C.) | Chemical Name |
|---|---|---|---|
| 67 | terbutryn | 104–105 | N-(1.1-dimethylethyl)-N'-ethyl-6-(methylthio)-1,3,5-triazine-2,4-diamine |
| 68 | triclopyr | 148–150 | [(3,5,6-trichloro-2-pyridinyl)oxy]acetic acid |
| 69 | 2,4-D | 140 | (2,4-dichlorophenoxy)acetic acid |
| 60 | 2,4-DB | 119–120 | 4-(2,4-dichlorophenoxy)-butanoic acid |
| 71 | triasulfuron | >100 | (3-(6-methoxy-4-methyl-1,3,5-triazin-2-yl)-1-[2-(2-chloroethoxy)phenylsulfonyl]urea |
| 72 | primisulfuron | >100 | [2-/3-(4,6-bis(difluoro-methoxypyrimidin-2-yl-ureidosulfonyl)benzoic acid methyl ester] |
| 73 | — | >100 | [2-/3-(4,6-bis(difluoro-methoxy)-pyrimidin-2-yl)-ureidosulfonyl)-benzoic acid methylester] |
| 74 | NC-311 | 170–172 | [5-pyrazolesulfonamide, N-[(4-methoxy-6-methyl-pyrimidine-2-yl)-amino-carbonyl]-4-methoxy-carbonyl-1-methyl-] |
| 75 | — | 160–162 | N-[[(4,6-dimethoxy-2-pyrimidinyl)amino]carbonyl]-3-(ethylsulfonyl)-2-pyridinesulfonamide |
| 76 | — | 152–159 | 2-[[[[(4,6-dimethoxy-2-pyrimidinyl)amino]carbonyl]-amino]sulfonyl]-N,N-dimethyl-3-pyridine-carboxamide |
| 77 | — | 204–206 | Methyl 2-[[[[[4-ethoxy-6-(methylamino)-1,3,5-triazin-2-yl]amino]carbonyl]amino]-sulfonyl]benzoate |
| FUNGICIDES | | | |
| 78 | carbendazim | 302–307 | methyl 2-benzimidazole-carbamate |
| 79 | thiuram | 146 | tetramethylthiuram disulfide |
| 80 | dodine | 136 | n-dodecylguanidine acetate |
| 81 | chloroneb | 133–135 | 1,4-dichloro-2,5-dimethoxy-benzene |
| 82 | cymoxanil | 160–161 | 2-cyano-N-ethylcarbamoyl-2-methoxyiminoacetamide |
| 83 | captan | 178 | N-trichloromethylthiotetra-hydrophthalamide |
| 84 | folpet | 177 | N-trichloromethylthio-phthalimide |
| 85 | thiophanate-methyl | 195 | dimethyl 4,4'-(o-phenylene)-bis(3-thioallophanate) |
| 86 | thiabendazole | 304–305 | 2-(thiazol-4-yl)benzimidazole |
| 87 | chlorothalonil | 240–241 | tetrachloroisophthalo-nitrile |
| 88 | dichloran | 195 | 2,6-dichloro-4-nitroaniline |
| 89 | captafol | 160–161 | cis-N-[1,1,2,2-tetrachloro-ethyl)thio]cyclohex-4-ene-1,2-dicarboximide |
| 90 | iprodione | 133–136 | 3-(3,5-dichlorophenyl)-N-(1-methylethyl)-2,4-dioxo-1-imidazolidine carboxamide |
| 91 | vinclozolin | 108 | 3-(3,5-dihclorophenyl)-5-ethenyl-5-methyl-2,4-oxazolidinedione |
| 92 | kasugamycin | 202–204 (DEC) | kasugamycin |
| 93 | triadimenol | 121–127 | beta-(4-chlorophenoxy)-α-(1,1-dimethylethyl)-1-H-1,2,4-triazol-1-ethanol |
| 94 | flutriafol | 130 | +-α-(2-fluorophenyl-α-(4-fluorophenyl)-1H-1,2,4-triazole-1-ethanol |
| 95 | flusilazol | 52–53 HCl 201–203 | 1-[[bis(4-fluorophenyl)-methylsilyl]methyl]-1H-1,2,4-triazole |
| 96 | hexaconazole | 111 | (+/−)-α-butyl-α-(2,4-di |

TABLE 1-continued

| Cmpd. No. | Common Name | m.p. (°C.) | Chemical Name |
|---|---|---|---|
| | | | chlorophenyl)-1H-1,2,4-triazole-1-ethanol |
| 97 | fenarimol | 117–119 | α-(2-chlorophenyl)-α-(4-chlorophenyl)-5-pyridinemethanol |
| BACTERICIDES | | | |
| 98 | oxytetracycline dihydrate | 181–182 (DEC) | oxytetracycline dihydrate |
| ACARICIDES | | | |
| 99 | hexathiazox | 108–109 | trans-5-(4-chlorophenyl)-N-cyclohexyl-4-methyl-2-oxo-3-thiazolidinecarboxamide |
| 100 | oxythioquinox | 169–170 | 6-methyl-1,3-dithiolo-[2,3-B]quinonolin-2-one |
| 101 | dienochlor | 122–123 | bis(pentachloro-2,4-cyclopentadien-1-yl) |
| 102 | cyhexatin | 245 | tricyclohexyltin hydroxide |
| INSECTICIDES | | | |
| 103 | carbofuran | 150–152 | methylcarbamic acid, ester with 2,3-dihydro-2,2-dimethyl-7-benzofuranol |
| 104 | carbaryl | 142 | methylcarbamic acid, ester with a-naphthol |
| 105 | thiodicarb | 173–174 | dimethyl N,N'-[thiobis-(N-methylimmo)carbonyloxy]]-bis[ethanimidothioate] |
| 106 | deltamethrin | 98–101 | α-cyano-3-phenoxybenzyl-cis-3-(2,2-dibromovinyl)-2,2-dimethylcyclopropane carboxylate |

The most common method for applying water insoluble pesticides is as fine aqueous dispersions which are sprayed onto the field or crop using ground or aerial spray rigs. The tablets of this invention combine a high level of physical integrity with rapid break-up in cold, hard water using minimal or no agitation while providing fine dispersions of active ingredient. Since the spray nozzles are typically protected against clogging by 50 mesh screens (U.S. mesh size), the dispersions must be fine enough to pass through this size screen without plugging it. This ability is characteristic of pesticide dispersions (i) delivered by the delivery system (ii) of this invention.

High physical integrity of the tablets is desirable so that the tablets themselves can withstand the tabletting operation and survive handling, packaging and shipping without breaking. An axial breaking strength of greater than about 2.0 kiloponds is generally necessary for a tablet to survive such treatment.

Rapid break-up in cold, hard water (greater than about 300 ppm as calcium carbonate) is desirable for the convenience of the growers who require quick turn-around times for the preparation of the dispersions. Generally the tablets of the invention disperse completely in less than 10 minutes, most in less than 5 minutes using even the very cold water drawn from wells in the early spring.

The tablets of the invention with these characteristics are obtained by the combination of the active agent with five inert ingredients: acid, base, dispersant, disintegrant and wetting agent.

It is substantially impossible to obtain rapid break-up of a tablet of substantially water-insoluble active ingredient in aqueous media without the use of effervescence. The reaction of the organic acid and carbonate or bicarbonate base affords carbon dioxide gas which aids in this respect.

A dispersant is required so that the particles of the active ingredient formed during the disintegration of the tablet remain separated in the cold, hard water.

The disintegrant allows the penetration of the water into the interior of the tablet through a wicking or swelling action. Common starch or cellulose-based disintegrants are unsuitable in agricultural applications as they typically form gels on the 50 mesh spray nozzle screens. Hence, the use of a water insoluble cross-linked polyvinylpyrrolidone.

A wetting agent is required to control the size of the carbon dioxide bubbles formed during the reaction of the acid and base. The wetting agent reduces the surface tension between the bubbles and the solid tablet resulting in the formation of smaller bubbles which readily detach from the tablet surface. As a consequence, the tablet remains submerged in the water for a longer period of time, thus improving contact of the entire tablet surface with water.

If a tablet floats immediately after being dropped in the water its top rapidly dries out and the reaction slows down there. This increases the time required for complete dispersion of active ingredient. When a tablet sinks, water wets the entire exterior of the tablet. Then, when the tablet floats to the surface (as a result of the buoyancy of the attached carbon dioxide bubbles when the tablet has partially dispersed and become lighter) the top remains wet so that effervescent reaction continues. Dispersion times for active ingredients formulated as described herein are very much more rapid than in formulations that produce tablets designed for flotation. To ensure that the tablet will sink initially, inert ingredients are employed that produce a tablet with a density greater than that of water (specific gravity greater than 1.00).

Inert ingredients up to 55% of the total weight of the composition can be employed. Inert fillers such as sugar or clay can be added as long as they do not affect the chemical stability of the active ingredient(s). Materials such as glidants, anti-adherents, and lubricants can also be employed to facilitate production in the tablet press. The amounts and types of such ingredients will be readily determinable by one skilled in the tabletting art given the disclosure herein.

The formulation ingredients (all solids) should be dry before being blended, milled and compacted. Drying at 45° to 60° C. for 16 hours in a vacuum oven is sufficient to reduce the water content of the premix to below about 0.5%. This is important so that residual moisture does not initiate the effervescence reaction during storage. The ingredients are typically ground and mixed in a mill, e.g., an air or hammermill. The ground premix is brushed through a 50 or 100 mesh (U.S.A. Standard Sieve Series) screen.

The average particle size of the ground premix should be in the range of 5 to 15 microns. If it is much smaller, the tablet will be strong, but will not break up very fast. If the premix is much larger, the dispersion will not be fine enough to pass a wet screen test used to indicate whether the dispersion will clog the spray nozzle and protective screen discussed previously.

The tablets can be prepared using conventional tablet-making equipment. Their diameter can vary from about ¼ inch or less, to 3 inches, depending on the tablet weight desired. Flat-faced, beveled-edge punches, with or without a breakline, produce attractive tablets.

To keep the tablet from sticking to the die or punch faces, a lubricant such as magnesium stearate or boric acid can be used. Such lubricants and anti-adherants can be brushed onto the die surface or incorporated into the formulation.

Tablets have been formed in a hydraulic press with a capacity of 40,000 pounds of force. Pressures between about 5,000 and 10,000 psi will produce strong tablets that break up rapidly. Break-up times are determined by dropping a tablet, typically 7 to 14 g, into about 800 to 1000 mL of water. The "end point" of final dispersion is easy to determine because the tablet floats to the surface as it loses weight shortly before it finally disperses.

The resultant dispersion is then poured through a nest of 50/100/200 mesh wet screens. A qualitative judgment is then made about the amount of material that is retained on each screen. A good tablet will leave just a "trace" on the 200 mesh screen, and the larger screens will be free of residue.

The strength of the tablet can be measured by a tester such as the Erweka Model TBH 28. The tablet is stood on end and the machine tip moves to the tablet along an axial path. The force to break the tablet in two is normally recorded in kiloponds (kp). Other units such as newtons (N) or Strong-cobbs (Sc) can also be used. Good tablets normally have strengths in the range of 2 to 10 kp.

The invention is illustrated by the following Examples.

EXAMPLE 1

The following ingredients were milled for 1 min in a Tekmar A 10 analytical laboratory mill. The premix was then passed through a 50 mesh screen and blended well. A 7 g tablet, 1⅜ in (3.49 cm) diameter, was made with a hand-operated precision hydraulic press.

| Ingredients | Concentration Weight Percent |
| --- | --- |
| trans-5-(4-chlorophenyl)-N-cyclohexyl-4-methyl-2-oxothiazolidine-3-carboxamide (insecticide) | 50 |
| Citric Acid | 12 |
| Sodium Bicarbonate | 25 |
| Lomar PWA | 10 |
| Polyplasdone XL-10 | 2 |
| Monawet MB-100 | 1 |

The tablet broke up completely in 25° C., hard water (420 ppm as $CaCO_3$) in 4 min, 11 sec. There was only a trace of residue on the 50 mesh wet screen and a trace on the 100 and 200 mesh screens.

EXAMPLE 2

A tablet was prepared from the following ingredients in the same manner as described in Example 1.

| Ingredients | Concentration Weight Percent |
| --- | --- |
| MBC (fungicide) | 52.1 |
| Citric Acid | 10.0 |
| Sodium Bicarbonate | 25.6 |
| Lomar PWA | 5.0 |
| Polyplasdone XL-10 | 1.0 |
| Monawet MB-100 | 1.0 |
| Boric Acid | 5.0 |
| Magnesium Stearate | 0.3 |

The tablet dispersed completely in 25° C. tap water in 3 min, 23 sec. There was no residue on the 50 mesh wet screen and only a trace on the 100 and 200 mesh screens. Its density was 1.25 g/cc.

EXAMPLE 3

The following ingredients were blended and hammermilled one time through a 0.032 in round-hole screen. A 7 g tablet, 1⅜ in diameter, was prepared on a hand-operated hydraulic press.

| Ingredients | Concentration Weight Percent |
| --- | --- |
| 3[[[[(4-methoxy-6-methyl-1,3,5-triazin-2-yl)amino]-carbonyl]amino]sulfonyl]-2-thiophene carboxylic acid, methyl ester | 52.1 |
| Citric Acid | 10.0 |
| Sodium Bicarbonate | 25.6 |
| Lomar PWA | 5.0 |
| Polyplasdone XL-10 | 1.0 |
| Monawet MP-100 | 1.0 |
| Boric Acid | 5.0 |
| Magnesium Stearate | 0.3 |

The tablet dispersed complete in 25° C. tap water in 2 min, 24 sec. There was no residue on the 50 mesh wet screen and only a trace on the 100 and 200 mesh screens. It remained submerged for 16 sec.

EXAMPLES 4 to 11

The following formulations were each milled for 1 min in a Tekmar A-10 analytical laboratory mill. A 7 g tablet, 1⅜ in (3.49 cm) diameter, was made from each premix with a hand-operated hydraulic press. The formulation used is shown below:

| Ingredients | Concentration Weight Percent |
| --- | --- |
| Active Ingredient | 52.1 |
| Citric Acid | 10.0 |
| Sodium Bicarbonate | 25.6 |
| Lomar PWA | 5.0 |
| Polyplasdone XL-10 | 1.0 |
| Monawet MP-100 | 1.0 |
| Boric Acid | 5.0 |
| Magnesium Stearate | 0.3 |

The density, strength, submerged and break up times are shown in Table 2 for eight active ingredients given by Compound number in Table 1. The times are shown as min:sec.

TABLE 2

| Ex. | Active Compound | Density g/cc | Strength kp | Time Submerged | Break-up Time |
| --- | --- | --- | --- | --- | --- |
| 4 | 23 | 1.29 | 3.56 | :34 | 2:32 |
| 5 | 75 | 1.28 | 3.26 | :30 | 2:17 |
| 6 | 76 | 1.23 | 3.16 | :27 | 3:31 |
| 7 | 24 | 1.27 | 4.58 | :52 | 2:17 |
| 8 | 4 | 1.30 | 3.97 | 1:10 | 3:09 |
| 9 | 11 | 1.28 | 3.16 | :26 | 2:13 |
| 10 | 77 | 1.31 | 4.68 | 1:32 | 3:20 |
| 11 | 63 | 1.28 | 3.56 | :38 | 2:23 |

EXAMPLE 12

The following ingredients were milled for 1 min and a 7 g tablet, 1⅜ in (3.49 cm) diameter, was prepared as described in Example 1.

| Ingredients | Concentration Weight percent |
| --- | --- |
| methyl 2-[[[[(4-methoxy-6-methyl-1,3,5-triazin-2-yl)-amino]carbonyl]amino]-sulfonyl]benzoate | 50 |
| Citric Acid | 11 |
| Sodium Bicarbonate | 32 |
| Lomar PWA | 5 |
| Polyplasdone XL-10 | 1 |
| Monawet MB-100 | 1 |

The tablet dispersed completely in 0° C., hard water (420 ppm as CaCO₃) in 3 min, 15 sec. The resultant dispersion passed through a wet 200 mesh screen with only a trace of residue.

EXAMPLE 13

A tablet from the following formulation was prepared as in Example 12.

| Ingredients | Concentration Weight percent |
| --- | --- |
| methyl 2-[[[[(4-methoxy-6-methyl-1,3,5-triazin-2-yl)-amino]carbonyl]amino]-sulfonyl]benzoate | 50 |
| Phthalic Acid | 14 |
| Sodium Bicarbonate | 22 |
| Lomar PWA | 10 |
| Polyplasdone XL-10 | 2 |
| Monawet MB-100 | 2 |

The tablet broke up completely in 25° C. tap water in 2 min, 35 sec. Its strength was 5.70 kiloponds and it left only a trace of material on a wet 200 mesh screen.

EXAMPLE 14

A tablet was prepared from the following formulation using the same procedure as in Example 12.

| Ingredients | Concentration Weight percent |
| --- | --- |
| methyl 2-[[[[(4-methoxy-6-methyl-1,3,5-triazin-2-yl)-amino]carbonyl]amino]-sulfonyl]benzoate | 50 |
| Succinic Acid | 12 |
| Sodium Carbonate | 24 |
| Lomar PWA | 10 |
| Polyplasdone XL-10 | 2 |
| Monawet MB-100 | 2 |

The 7 g tablet broke up in 25° C. tap water in 1 min, 26 sec. It left no residue on a wet 200 mesh screen.

EXAMPLE 15

The following ingredients were blended and hammermilled twice through a 0.032 in round hole screen. A 7.2 g tablet, 1⅜ in (3.49 cm) diameter was prepared in a hand-operated Preco hydraulic press.

| Ingredients | Concentration Weight percent |
| --- | --- |
| ethyl 2-[[[[(4-chloro-6-methoxy-2-pyrimidinyl)amino]-carbonyl]amino]sulfonyl]-benzoate | 51.0 |
| Fumaric Acid | 7.0 |
| Sodium Bicarbonate | 12.5 |
| Polyfon H | 7.5 |
| Polyplasdone XL-10 | 2.0 |
| Monawet MB-100 | 1.75 |
| Sipernat 50-S (precipitated silica) | 1.25 |
| Diluex FG (attapulgite clay) | 12.0 |
| Avicel PH 101 (microcrystalline cellulose) | 5.0 |

The tablet broke up in 50 sec in room temperature water when stirred gently with a spatula. It gave no residue on a wet 60 mesh screen and only a trace on a 200 mesh screen.

EXAMPLES 16 TO 33

By the general procedure of Example 1, tablet formulations can be made whereby the active ingredient pesticide is as described hereafter and the complementary delivery system components are within the following ranges:

(a) about 5% to 20% of a dibasic or tribasic organic carboxylic acid or a mixture thereof;
(b) about 7% to 50% of an ammonium or alkali metal carbonate or bicarbonate or a mixture thereof;
(c) about 0.5% to 20% of a dispersant;
(d) about 0.1% to 5% of water insoluble cross-linked polyvinylpyrrolidone; and
(e) about 0.1% to 5% of an anionic or nonionic wetting agent.

EXAMPLE 16

The pesticide, described in more detail in U.S. Pat. No. 4,127,405, is a compound of the formula:

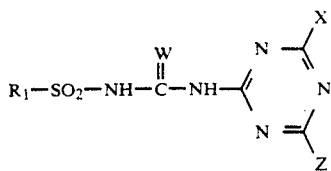

wherein $R_1$ is

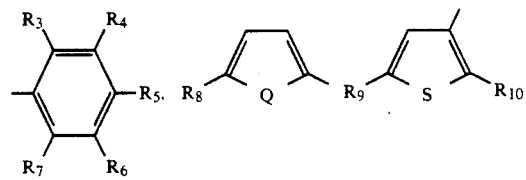

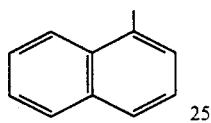

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, $CH_3S$— or $CH_3OCH_2$—; and Z is methyl or methoxy, or their agriculturally suitable salts.

EXAMPLE 17

The pesticide, described in more detail in U.S. Pat. No. 4,394,506, is a compound of the formula: N-(heterocyclicaminocarbonyl)arylsulfonamides in which the aryl radical is substituted in the 2-position by a carboxy radical, ester, thioester, or amide thereof; e.g., N-[(4,6-dimethylpyrimidin-2yl)aminocarbonyl]methoxycarbonyl]benzenesulfonamide or N-[(4,6-dimethoxy-1,3,5-triazin-2-yl)aminocarbonyl]-2-methoxycarbonylbenzenesulfonamide.

EXAMPLE 18

The pesticide, described in more detail in U.S. Pat. No. 4,481,029, is a compound of the formula:

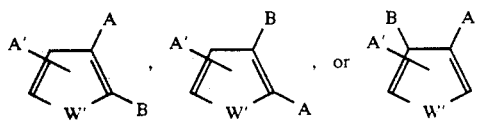

wherein

W' is O or S;

A' is H, Cl, Br, $C_1$-$C_4$ alkyl, $OCH_3$, $NO_2$ or $CF_3$;

A is

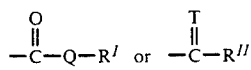

where

Q is O, S or

T is O or

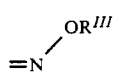

where $R^{III}$ is H, $C_1$-$C_4$ alkyl or $C_3$-$C_4$ alkenyl; when Q is O or S then $R^I$ is $C_1$-$C_6$ alkyl $C_3$-$C_6$ alkenyl; $C_3$-$C_6$ alkynyl; $C_2$-$C_6$ alkyl substituted with 1-3 Cl, F or Br, or one of CN or $OCH_3$; $C_3$-$C_6$ alkenyl substituted with 1-3 Cl; $C_3$-$C_6$ alkynyl substituted with Cl; $C_5$-$C_6$ cycloalkyl; cyclohexenyl; cyclohexyl substituted with 1-3 $CH_3$; $C_4$-$C_7$ cycloalkylalkyl or

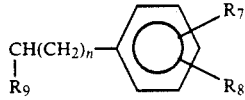

where $R_7$ and $R_8$ are independently H, Cl, $CH_3$ or $OCH_3$;

n is 0 or 1; and $R_9$ is H or $CH_3$;

$R_1$ is

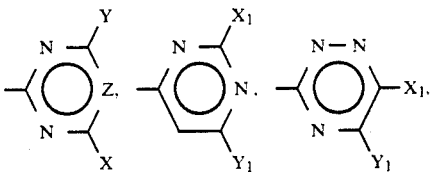

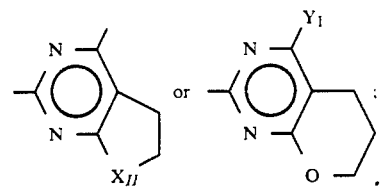

where

Z is N, CH or C—F;

X=H, Cl, —$CH_3$, —$OCH_3$ or —$OCH_2CH_3$;

Y=H, Cl, $C_1$-$C_4$ substituted alkyl; with the proviso that when X and Y are both H, then $R^I$ and $R^{II}$ are less than 5 carbons;

$X_1$=H, Cl, $OCH_3$, $OCH_2CH_3$ or $CH_3$;

$Y_1$=H, OCH$_3$ or CH$_3$; and
$X_{II}$=O or CH$_2$ and further provided that when A contains greater than 5 carbon atoms, then Y contains $\leq$4 carbon atoms, and their agriculturally suitable salts;

all other substituents being as defined in U.S. Pat. No. 4,481,029.

EXAMPLE 19

The pesticide, described in more detail in U.S. Pat. No. 4,435,205, is a compound of the formula:

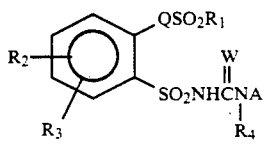

where
W is O or S;
Q is O or NR$_5$;
R$_1$ is C$_1$-C$_4$ alkyl, C$_1$-C$_4$ alkyl substituted with 1-3 atoms of F, Cl or Br, CH$_2$CH$_2$OCH$_3$, CH$_2$CH$_2$CH$_2$OCH$_3$ or

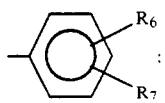

R$_2$ is H, F, Cl, Br, OCH$_3$, NO$_2$, CF$_3$ or C$_1$-C$_2$ alkyl;
R$_3$ is H, F, Cl, Br or CH$_3$;
R$_4$ is H, CH$_3$ or OCH$_3$;
R$_5$ is C$_1$-C$_4$ alkyl;
R$_6$ and R$_7$ are independently H, F, Cl, Br, CH$_3$, CF$_3$, NO$_2$ or OCH$_3$;
A is

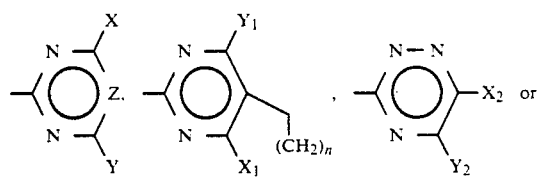

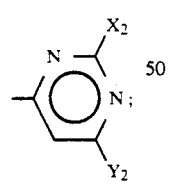

X is NH$_2$, N(CH$_3$)$_2$, NHCH$_3$, C$_1$-C$_4$ alkyl substituted with 1-3 atoms of F, Cl or Br, CH$_2$OCH$_3$, CH$_2$OCH$_2$CH$_3$, C$_1$-C$_4$ alkoxy, C$_1$-C$_2$ alkylthio, C$_3$-C$_4$ alkenyloxy, C$_3$-C$_4$ alkynyloxy, OCH$_2$CH$_2$OCH$_3$ or C$_2$-C$_4$ alkoxy substituted with 1-3 atoms of F, Cl or Br;
n is 1 or 2;
Y is H, CH$_3$, OCH$_3$ or Cl;
X$_1$ is O or CH$_2$;
Y$_1$ is H, CH$_3$, OCH$_3$ or Cl;
X$_2$ and Y$_2$ are independently CH$_3$ or OCH$_3$; and
Z is CH, N, CCH$_3$, CBr, CCl, CF, Cl, CC$_2$H$_5$, CCH$_2$CH$_2$Cl or CCH$_2$CH=CH$_2$.

EXAMPLE 20

The pesticide, described in more detail in U.S. Pat. No. 4,420,325, is a compound of the formula:

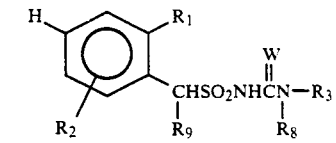

wherein
R$_1$ is F, Cl, Br, CF$_3$, C$_1$-C$_3$ alkyl, NO$_2$, CO$_2$R$_4$, SO$_2$R$_5$, SO$_2$NR$_6$R$_7$, SO$_2$N(OCH$_3$)CH$_3$, SO$_2$OCH$_2$CF$_3$, OSO$_2$R$_5$ or CH$_2$L;
L is SO$_2$NR$_6$R$_7$, OCH$_3$, OC$_2$H$_5$, CO$_2$H$_5$, CO$_2$CH$_3$ or CO$_2$C$_2$H$_5$;
R$_2$ is H, Cl, Br, F, CF$_3$ or OCH$_3$;
R$_4$ is C$_1$-C$_3$ alkyl, CH$_2$CH=CH$_2$, CH$_2$CH$_2$Cl, or CH$_2$CH$_2$OCH$_3$;
R$_5$ is C$_1$-C$_3$ alkyl or CF$_3$;
R$_6$ and R$_7$ are independently C$_1$-C$_3$ alkyl;
R$_8$ is H or CH$_3$;
R$_9$ is H or C$_1$-C$_3$ alkyl;
R$_3$ is

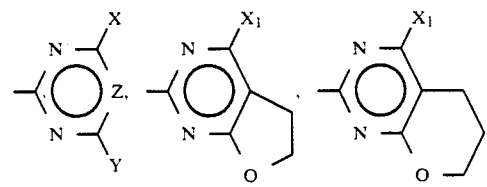

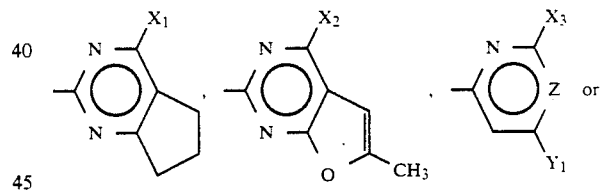

W is O or S;
X is CH$_3$, OCH$_3$ or Cl;
Y is CH$_3$, C$_2$H$_5$, OCH$_3$, OC$_2$H$_5$, CH$_2$OCH$_3$, NH$_2$, NHCH$_3$ or N(CH$_3$)$_2$;
Z is CH or N;
X$_1$ is H, Cl, CH$_3$, OCH$_3$ or OC$_2$H$_5$;
X$_2$ is CH$_3$, C$_2$H$_5$, OCH$_3$ or OC$_2$H$_5$;
X$_3$ is CH$_3$ or OCH$_3$; and
Y$_1$ is CH$_3$ or OCH$_3$;
and their agriculturally suitable salts.

EXAMPLE 21

The pesticide, described in more detail in U.S. Pat. No. 4,514,211, is a compound of the formula:

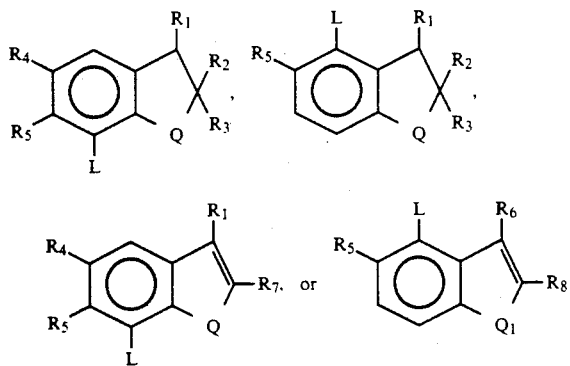

wherein
Q is O, S, SO or $SO_2$;
$Q_1$ is O, S or $SO_2$;
L is

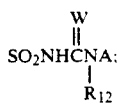

$R_1$ is H or $C_1$-$C_4$ alkyl;
$R_2$ is H or $C_1$-$C_4$ alkyl;
$R_3$ is H or $CH_3$;
$R_4$ is H, Cl, $CH_3$, $CF_3$, $OCH_3$, Br, F, $SCH_3$ or $OCF_2H$;
$R_5$ is H, $CH_3$, Cl, Br, $NO_2$, $CO_2R_7$, $SO_2R_8$, $OSO_2R_9$, $SO_2NR_{10}R_{11}$, F, $CF_3$, $SCH_3$, $OCF_2H$ or $SO_2N(OCH_3)CH_3$;
$R_6$ is H, Cl, Br or $C_1$-$C_4$ alkyl;
$R'_6$ is H, $CH_3$, Cl or Br;
$R_7$ is $C_1$-$C_3$ alkyl, $CH_2CH=CH_2$, $CH_2CH_2OCH_3$ or $CH_2CH_2Cl$;
$R_8$ is $C_1$-$C_3$ alkyl;
$R_9$ is $C_1$-$C_3$ alkyl or $CF_3$;
$R_{10}$ and $R_{11}$ are independently $C_1$-$C_2$ alkyl;
$R_{12}$ is H or $CH_3$;
W is O or S;
A is

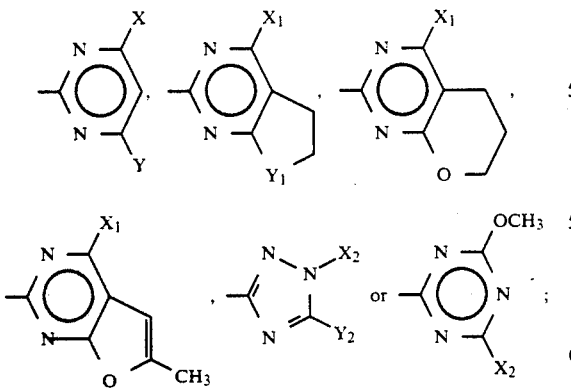

X is H, $CH_3$, $OCH_3$, Cl, F, $OCF_2H$ or $SCF_2H$;
Y is $CH_3$, $OCH_3$, $OC_2H_5$, $CH_2OCH_3$, $NH_2$, $NHCH_3$, $N(CH_3)_2$, $CH(OCH_3)_2$, $CH(OCH_2CH_3)_2$, $C_2H_5$, $CF_3$, $CH_2=CHCH_2O$, $CH\equiv CCH_2O$, $CF_3CH_2O$, $OCH_2CH_2Cl$, $OCH_2CH_2Br$, $OCH_2CH_2F$, CN, $CH_2OCH_2CH_3$, $OCH_2CH_2OCH_3$ or $GCF_2T$ wherein G is O or S and T is H, CHClF, CHBrF, $CF_2H$ or $CHFCF_3$;
Z is CH, N, $CCH_3$, $CC_2H_5$, CCl or CBr;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $C_2H_5$, $CH_3$, $OCH_3$, $OC_2H_5$, $SCH_3$ or $SC_2H_5$; and
$X_3$ is $CH_3$ or $OCH_3$.

EXAMPLE 22

The pesticide, described in more detail in U.S. Pat. No. 4,547,215, is a compound of the formula:

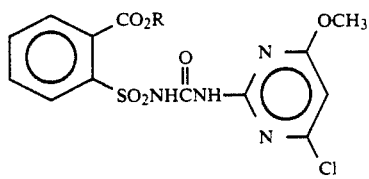

wherein
R is $C_2H_5$ or $CH(CH_3)_2$;
and their agriculturally suitable salts.

EXAMPLE 23

The pesticide, described in more detail in U.S. Pat. No. 4,548,638, is a compound of the formula:

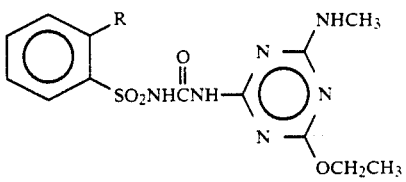

wherein
R is $CO_2CH_3$, $CO_2CH_2CH_3$, $CO_2CH_2CH_2CH_3$, $CO_2CH_2CH=CH_2$, $CO_2CH(CH_3)$, $CO_2CH_2CH_2Cl$, $SO_2N(CH_3)_2$ or $OSO_2CH_3$.

EXAMPLE 24

The pesticide, described in more detail in U.S. Pat. No. 4,479,821, is a compound of the formula:

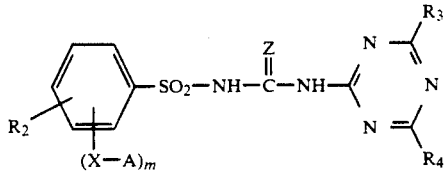

wherein
A is a $C_1$-$C_6$ alkyl radical which is substituted by $C_1$-$C_4$ alkoxy, $C_1$-$C_4$ alkylthio, $C_1$-$C_4$ alkylsulfinyl or $C_1$-$C_4$ alkylsulfonyl;
X is oxygen, sulfur, a sulfinyl or sulfonyl bridge;
Z is oxygen or sulfur;
m is 1 or 2;
$R_2$ is hydrogen, halogen, $C_1$-$C_5$ alkyl, $C_2$-$C_5$ alkenyl, $C_1$-$C_4$ haloalkyl, or a radical $-Y-R_5$, $-COOR_6$, $-NO_2$ or $-CO-NR_7R_8$;
$R_3$ and $R_4$, each independently of the other, are hydrogen, $C_1$-$C_4$ alkyl, $C_1$-$C_4$ alkoxy, $C_1$-$C_4$ alkylthio, $C_1$–$C_4$ haloalkyl, halogen or alkoxyalkyl of at most 4 carbon atoms;

$R_5$ and $R_6$, each independently of the other, are $C_1$–$C_5$ alkyl, $C_2$–$C_5$ alkenyl or $C_2$–$C_6$ alkynyl;

$R_7$ and $R_8$, each independently of the other, are hydrogen, $C_1$–$C_5$ alkyl, $C_2$–$C_5$ alkenyl or $C_2$–$C_6$ alkynyl; and Y is oxygen, sulfur, a sulfinyl or sulfonyl bridge, and salts of these compounds.

EXAMPLE 25

The pesticide, described in more detail in U.S. Pat. No. 4,566,898, is a compound of the formula:

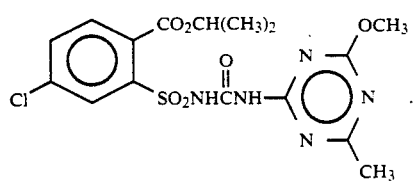

EXAMPLE 26

The pesticide, described in more detail in U.S. Pat. No. 4,435,206, is a compound of the formula:

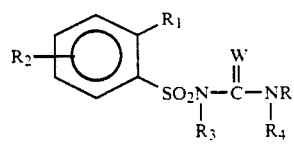

wherein
R is

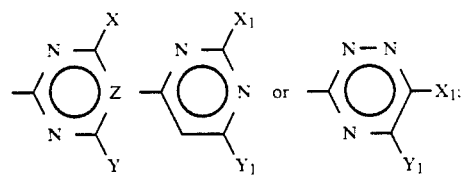

$R_1$ is H, Cl, Br, F, $C_1$–$C_4$ alkyl, $C_1$–$C_4$ alkoxy, $C_1$–$C_4$ alkylthio, $NO_2$, $CF_3$, $COOR_5$ or $SO_2NR_6R_7$;
$R_2$ is H, Cl, Br or $CH_3$;
$R_3$ and $R_4$ are independently H or $CH_3$;
$R_5$ is $C_1$–$C_6$ alkyl, $C_3$–$C_6$ alkenyl, $CH_2CH_2OCH_3$, $CH_2CH_2OCH_2CH_3$, $CH_2CH_2CH_2OCH_3$ or $CH_2CH_2Cl$;
$R_6$ and $R_7$ are independently $CH_3$ or $CH_3CH_2$;
W is oxygen or sulfur;
X is $CH_3$, $-OCH_3$ or $-OCH_2CH_3$;
Y is H, Cl, $CH_3$, $CF_3$, $-NHCH_3$, $-N(CH_3)_2-$, $-CH_2OR_8$, $-CH_2CH_2OR_8$, $-OCH_2CF_3$ or $VR_6$;
Z is CH or N;
V is oxygen or sulfur;
$R_8$ is $CH_3$, $CH_3CH_2-$, $CH_2CO_2R_8$, $-CH_2CH_2OR^6$, $C(CH_3)HCO_2R_8$ or $CH_2CH_2CO_2R_8$;
$Y_1$ is H, $CH_3$ or $OCH_3$; and
$X_1$ is H, Cl, $-OCH_3$, $-OCH_2CH_3$ or $CH_3$;
and agricultural salts thereof.

EXAMPLE 27

The pesticide, described in more detail in U.S. Pat. No. 4,514,212, is a compound of the formula:

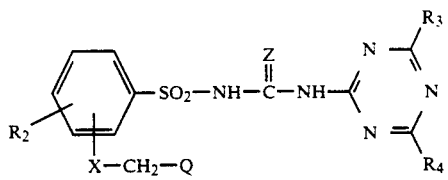

and the salts thereof with amines, alkali metal or alkaline earth metal bases or with quaternary ammonium bases wherein:

Q is fluorine, fluoromethyl, chloromethyl, trichloromethyl, 1,2-dichloroethyl, 1,2-dibromoethyl, 1,2-dichloropropyl, 1,2-dibromopropyl, 1,2-dibromoisobutyl, 1,2-dichloro-1-methyl-ethyl or 1,2-dibromo-1-methylethyl;

X is oxygen, sulfur, a sulfinyl or sulfonyl bridge;
Z is oxygen or sulfur;
$R_2$ is hydrogen, halogen, $C_1$–$C_5$ alkyl, $C_2$–$C_5$ alkenyl, $C_1$–$C_4$ haloalkyl, or a radical $-Y-R_5$, $-COOR_6$, $-NO_2$ or $-CO-NR_7-R_8$;

$R_3$ and $R_4$, each independently of the other, are hydrogen, $C_1$–$C_4$ alkyl, $C_1$–$C_4$ alkoxy, $C_1$–$C_4$ alkylthio, $C_1$–$C_4$ haloalkyl, halogen or alkoxyalkyl of at most 4 carbon atoms;

$R_5$ and $R_6$, each independently of the other, are $C_1$–$C_5$ alkyl, $C_2$–$C_5$ alkenyl or $C_2$–$C_6$ alkynyl;

$R_7$ and $R_8$, each independently of the other, are hydrogen, $C_1$–$C_5$ alkyl, $C_2$–$C_5$ alkenyl or $C_2$–$C_6$ alkynyl; and Y is oxygen, sulfur, a sulfinyl or sulfonyl bridge.

EXAMPLE 28

The pesticide, described in more detail in U.S. Pat. No. 4,478,635, is a compound of the formula:

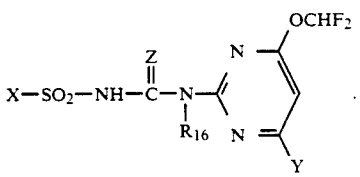

wherein
X is a radical of the formula:

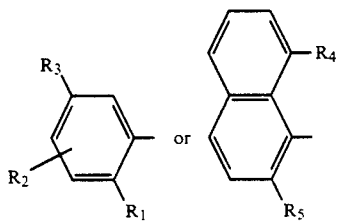

Y is $C_1$–$C_3$ alkyl, $C_1$–$C_3$ haloalkyl, $C_1$–$C_3$ alkoxy, $C_1$–$C_3$ haloalkoxy, $C_2$–$C_3$ alkoxyalkyl, $C_1$–$C_3$ alkylthio, halogen or $-NR_{16}R_{17}$;
Z is oxygen or sulfur;

$R_1$ is hydrogen, halogen, cyano, nitro, $C_1$-$C_4$ haloalkyl, $C_1$-$C_4$ alkyl, $C_1$-$C_4$ alkoxy, —CO—$R_6$, —$NR_7R_8$, —$S(O)_m$—$C_1$-$C_4$ alkyl or —$SO_2R_9$;

$R_2$ is hydrogen, fluorine, chlorine, bromine, nitro, trifluoromethyl, —$NR_{20}R_{21}$, methyl, ethyl, methoxy, ethoxy or —$S(O)_m$—$C_1$-$C_4$ alkyl;

$R_3$ is hydrogen, fluorine, chlorine, bromine, amino, nitro or methoxy;

$R_6$ is hydrogen, $C_1$-$C_4$ alkyl, $C_1$-$C_3$ alkenyloxy, $C_3$-$C_5$ alkynyloxy, $C_1$-$C_4$ haloalkyl, $C_1$-$C_5$ alkylthio, phenoxy, benzyloxy, —$NR_{10}R_{11}$ or $C_1$-$C_5$ alkoxy which is unsubstituted or substituted by 1 to 3 halogen atoms or $C_1$-$C_3$ alkoxy;

$R_7$ is hydrogen, methoxy, ethoxy, $C_1$-$C_4$ alkyl or —CO—$R_{12}$;

$R_8$ is hydrogen or —CO—$R_{12}$;

$R_9$ is an —O—$R_{13}$ or —$NR_{14}R_{15}$ group;

$R_{11}$ is $C_1$-$C_4$ alkyl which is unsubstituted or substituted by 1 to 3 halogen atoms, or is phenyl or benzyl;

$R_{12}$ is hydrogen, $C_1$-$C_4$ alkyl or $C_1$-$C_4$ alkoxy; and m is 0, 1 or 2;

and $R_4$ has the same meaning as $R_2$; $R_5$ has the same meaning as $R_1$; $R_{10}$, $R_{11}$, $R_{14}$ and $R_{20}$ each have the same meaning as $R_7$; and $R_{12}$, $R_{15}$, $R_{16}$, $R_{17}$ and $R_{21}$ each have the same meaning as $R_8$.

EXAMPLE 29

The pesticide, described in more detail in U.S. Pat. No. 4,634,465, is a compound of the formula:

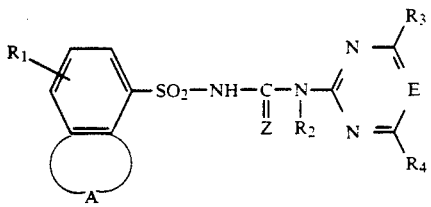

wherein

Z is oxygen or sulfur;

E is nitrogen or =C—;

$R_1$ is hydrogen, halogen, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxycarbonyl, $C_1$-$C_4$ alkylthio, $C_1$-$C_4$ alkylsulfinyl, $C_1$-$C_4$ alkylsulfonyl or $C_2$-$C_5$ alkoxyalkoxy;

$R_2$ is hydrogen, $C_1$-$C_4$ alkyl or $C_1$-$C_3$ alkoxy;

$R_3$ and $R_4$, each independently of the other, are hydrogen, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy or —$NR_5R_6$, wherein $R_5$ and $R_4$ are hydrogen or $C_1$-$C_4$ alkyl; and A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or —$SO_2$— group.

EXAMPLE 30

The pesticide, described in more detail in EPA-202,830, is: 2-[[N-(4-methoxy-6-methyl-1,3,5-triazin-2-yl)-N-methylaminocarbonyl]aminosulfonyl]benzoic acid, methyl ester.

EXAMPLE 31

The pesticide, described in more detail in EPA-237,292, is a compound of the formula:

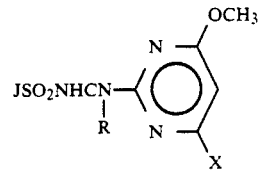

wherein

J is

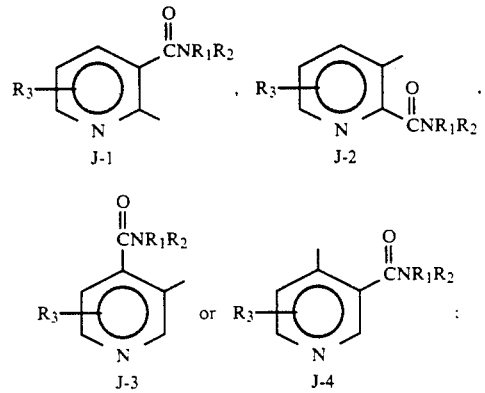

R is H or $CH_3$;

$R_1$ is H or $C_1$-$C_3$ alkyl;

$R_2$ is $C_1$-$C_3$ alkyl or $C_1$-$C_2$ alkoxy; or $R_1$ and $R_2$ may be taken together to form —$(CH_2)_n$—, wherein n is 2, 3 or 4;

$R_3$ is H, Cl, F, Br, $CH_3$, $CF_3$, $OCH_3$ or $OCF_2H$; and

X is $CH_3$, $CH_2F$, $CH_2CH_3$, $OCH_3$, $OCH_2CH_3$, Cl, $OCF_2H$ or $CH_2OCH_3$.

EXAMPLE 32

The pesticide, described in more detail in EPA-87,780, is a compound of the formula:

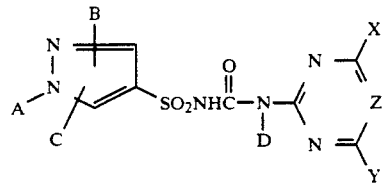

wherein

A represents a hydrogen atom, a $C_1$-$C_8$ alkyl group or a phenyl group which may be substituted with $C_1$-$C_8$ alkyl groups, halogen atoms or nitro groups;

B and C represent independently hydrogen atoms, halogen atoms, nitro groups, $C_1$-$C_8$ alkyl groups, arylalkyl groups, $C_1$-$C_8$ alkoxy groups, haloalkyl groups, —$CO_2R$ [where R is a hydrogen atom, a $C_1$-$C_8$ alkyl group, an allyl group or a propargyl group), —$CONR_1R_2$ (where $R_1$ is a hydrogen atoms, a $C_1$-$C_8$ alkyl group or a phenyl group, $R_2$ is a hydrogen atom or a $C_1$-$C_8$ alkyl group, or $R_1$ and $R_2$ taken together may represent —($CH_2$)$_m$— (m is 4, 5 or 6), —$CH_2CH_2OCH_2CH_2$— or —$CH_2CH_2N(CH_3)CH_2CH_2$—], —$S(O)_nR_3$ (where $R_3$ is a $C_1$-$C_8$ alkyl group, a phenyl group or an arylalkyl group and n is 0, 1 or 2), —$SO_2NR_4R_5$ [where $R_4$ is a $C_1$-$C_8$ alkyl group, $R_5$ is a hydrogen atom or a $C_1$-$C_8$ alkyl group, or $R_4$ and $R_5$ taken together may represent —($CH_2$)$_p$— (p is 4, 5 or 6), —$CH_2CH_2OCH_2CH_2$— or —$CH_2CH_2N(CH_3)CH_2CH_2$—] or a phenyl group which may be substituted with $C_1$-$C_8$ alkyl groups, halogen atoms or nitro groups; D represents a hydrogen atom or a $C_1$-$C_8$ alkyl group; X and Y represent independently hydrogen atoms, halogen atoms, $C_1$-$C_8$ alkyl groups, $C_1$-$C_8$ alkoxy groups, $C_1$-$C_8$ alkoxyalkyl groups, —$CF_3$ groups, $C_1$-$C_8$ haloalkoxy groups, alkylamino groups, dialkylamino groups,

(where $R_6$ and $R_7$ each represent hydrogen atoms or $C_1$-$C_8$ alkyl groups) or either X or Y may form a five-membered ring containing an oxygen atom together with X; and X represents a nitrogen atom or C—$R_8$ (where $R_8$ represents a hydrogen atom, a haloalkyl group or may form a five-membered ring containing an oxygen atom together with X or Y).

EXAMPLE 33

The pesticide, described in more detail in U.S. Pat. No. 4,710,221, is a compound of the formula:

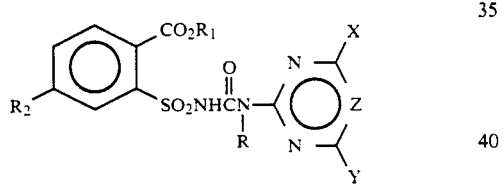

wherein
R is H or $CH_3$;
$R_1$ is $C_1$-$C_3$ alkyl, $C_3$-$C_4$ alkoxyalkyl, $C_2$-$C_4$ haloalkyl, $C_3$-$C_4$ alkenyl or $C_3$-$C_4$ alkynyl;
$R_2$ is $C_2$-$C_6$ alkoxy, $C_3$-$C_6$ cycloalkoxy, $C_4$-$C_6$ cycloalkylalkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_2$-$C_4$ alkoxyalkoxy, $C_2$-$C_4$ haloalkoxyalkoxy, $C_2$-$C_4$ alkylthioalkoxy, $C_2$-$C_4$ haloalkylthioalkoxy, $C_2$-$C_4$ alkylsulfinylalkoxy, $C_2$-$C_4$ haloalkylsulfinylalkoxy, $C_2$-$C_4$ alkylsulfonylalkoxy, $C_2$-$C_4$ haloalkylsulfonylalkoxy, $C_2$-$C_4$ cyanoalkoxy, $OCH_2C(O)CH_3$, $OCH_2CH_2C(O)CH_3$, $C_2$-$C_4$ aminoalkoxy, $C_1$-$C_8$ alkylthio, $C_3$-$C_6$ cycloalkylthio, $C_4$-$C_6$ cycloalkylalkylthio, $C_1$-$C_6$ haloalkylthio, $C_2$-$C_6$ alkenylthio, $C_2$-$C_6$ haloalkenylthio, $C_3$-$C_6$ alkynylthio, $C_3$-$C_6$ haloalkynylthio, $C_2$-$C_4$ alkoxyalkylthio, $C_2$-$C_4$ haloalkoxyalkylthio, $C_2$-$C_4$ alkylthioalkylthio, $C_2$-$C_4$ haloalkylthioalkylthio, $C_2$-$C_4$ cyanoalkylthio, $SCH_2C(O)CH_3$, $SCH_2CH_2C(O)CH_3$, $C_2$-$C_4$ aminoalkylthio, $SC_6H_5$, $SCH_2C_6H_5$, $C_1$-$C_8$ alkylsulfinyl, $C_3$-$C_6$ cycloalkylsulfinyl, $C_4$-$C_6$ cycloalkylalkylsulfinyl, $C_1$-$C_8$ haloalkylsulfinyl, $C_2$-$C_6$ alkenylsulfinyl, $C_2$-$C_6$ haloalkenylsulfinyl, $C_3$-$C_6$ alkynylsulfinyl, $C_3$-$C_6$ haloalkynylsulfinyl, $C_2$-$C_4$ alkoxyalkylsulfinyl, $C_2$-$C_4$ haloalkoxyalkylsulfinyl, $C_2$-$C_4$ cyanoalkylsulfinyl, $S(O)CH_2C(O)CH_3$, $S(O)CH_2CH_2C(O)CH_3$, $C_2$-$C_4$ aminoalkylsulfinyl, $C_2$-$C_8$ alkylsulfonyl, $C_3$-$C_6$ cycloalkylsulfonyl, $C_4$-$C_6$ cycloalkylalkylsulfonyl, $C_1$-$C_8$ haloalkylsulfonyl, $C_2$-$C_6$ alkenylsulfonyl, $C_2$-$C_6$ haloalkenylsulfonyl, $C_3$-$C_6$ alkynylsulfonyl, $C_3$-$C_6$ haloalkynylsulfonyl, $C_2$-$C_4$ alkoxyalkylsulfonyl, $C_2$-$C_4$ haloalkoxyalkylsulfonyl, $C_2$-$C_4$ cyanoalkylsulfonyl, $SO_2CH_2C(O)CH_3$, $SO_2CH_2CH_2C(O)CH_3$, $C_2$-$C_4$ aminoalkylsulfonyl, $CH_2F$, $CHF_2$, $CH_2Cl$, $CHCl_2$, $CH_2Br$, $CHBr_2$, $C_2$-$C_6$ alkyl substituted with 1-3 atoms of F, Cl or Br, $C_2$-$C_6$ alkenyl, $C_2$-$C_6$ haloalkenyl, C≡CH, $C_2$-$C_6$ haloalkynyl, $OC(O)C_1$-$C_4$ alkyl, $CH_2C(O)NR_aR_b$, $NHCH_3$, $NR_bR_c$ or $C_1$-$C_4$ alkyl substituted with $C_1$-$C_4$ alkoxy, $C_3$-$C_4$ cycloalkoxy, cyclopropylmethoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_2$-$C_4$ alkoxyalkoxy, $C_2$-$C_4$ aminoalkoxy, $C_1$-$C_4$ alkylcarbonyloxy, $C_1$-$C_4$ haloalkylcarbonyloxy, $C_1$-$C_4$ carbamoyloxy, $C_1$-$C_4$ alkoxycarbonyloxy, OH, OP(O) ($OC_1$-$C_2$ alkyl)$_2$, $C_1$-$C_4$ alkylsulfonyloxy, $C_1$-$C_2$ haloalkylsulfonyloxy, $OSi(CH_3)_3$, $OSi(CH_3)_2C(CH_3)_3$, $C_1$-$C_4$ alkylthio, $C_3$-$C_4$ cycloalkylthio, cyclopropylmethylthio, $C_1$-$C_4$ haloalkylthio, $C_2$-$C_4$ alkenylthio, $C_2$-$C_4$ haloalkenylthio, $C_3$-$C_4$ alkynylthio, $C_3$-$C_4$ haloalkynylthio, $C_2$-$C_4$ alkoxyalkylthio, $C_2$-$C_4$ aminoalkylthio, SH, SP(O) ($OC_1$-$C_2$ alkyl)$_2$, $C_1$-$C_4$ alkylsulfinyl, $C_3$-$C_4$ cycloalkylsulfinyl, cyclopropylmethylsulfinyl, $C_1$-$C_4$ haloalkylsulfinyl, $C_2$-$C_4$ alkenylsulfinyl, $C_2$-$C_4$ haloalkenylsulfinyl, $C_3$-$C_4$ alkynylsulfinyl, $C_3$-$C_4$ haloalkynylsulfinyl, $C_2$-$C_4$ alkoxyalkylsulfinyl, $C_2$-$C_4$ aminoalkylsulfinyl, $C_1$-$C_4$ alkylsulfonyl, $C_3$-$C_4$ cycloalkylsulfonyl, cyclopropylmethylsulfonyl, $C_1$-$C_4$ haloalkylsulfonyl, $C_2$-$C_4$ alkenylsulfonyl, $C_2$-$C_4$ haloalkenylsulfonyl, $C_3$-$C_4$ alkynylsulfonyl, $C_3$-$C_4$ haloalkynylsulfonyl, $C_2$-$C_4$ alkoxyalkylsulfonyl or $C_2$-$C_4$ aminoalkylsulfonyl;
$R_a$ and $R_b$ are independently H or $C_1$-$C_3$ alkyl;
$R_c$ is $C_2$-$C_4$ alkyl, cyclopropylmethyl, $C_2$-$C_4$ cyanoalkyl, $CH_2C(O)CH_3$, $CH_2CH_2C(O)CH_3$, $C_1$-$C_4$ haloalkyl, $C_3$-$C_4$ alkenyl, $C_3$-$C_4$ haloalkenyl, $C_3$-$C_4$ alkynyl, $C_3$-$C_4$ haloalkynyl, $C_1$-$C_4$ alkyl substituted with $C_1$-$C_4$ alkoxy, $C_1$-$C_4$ alkylthio, $C_1$-$C_4$ alkylsulfinyl, $C_1$-$C_4$ alkylsulfonyl, OH, $NH_2$, $NHCH_3$ or $N(CH_3)_2$;
X is $CH_3$, $OCH_3$, $OC_2H_5$, Cl or Br;
Y is $C_1$-$C_2$ alkyl, $C_1$-$C_2$ alkoxy, $OCH_2CH_2F$, $OCH_2CHF_2$, $OCH_2CF_3$, $NHCH_3$ or $N(CH_3)_2$; and
Z is CH or N; and
their agriculturally suitable salts.
What is claimed is:
1. A tablet formulation consisting essentially of, by total weight of the formulated composition:
(i) 20% to 75% of a pesticide or growth regulant having a melting point of at least 100° C. and a water solubility at 20° C. of no more than 5% by weight, and
(ii) 25% to 80% of a delivery system characterized by a panel of components complementary to the pesticide of (i) that consists essentially of the following components:
(a) 5% to 20% of a dibasic or tribasic organic carboxylic acid or a mixture thereof;

(b) 7% to 50% of an ammonium or alkali metal carbonate or bicarbonate or a mixture thereof;

(c) 0.5% to 20% of a dispersant, (d) about 0.1% to 5% of water-insoluble cross-linked polyvinylpyrrolidone, and (e) 0.1% to 5% of an anionic or nonionic wetting agent;

the formulation forming a dispersion in water, fine enough to pass a 50 mesh screen without clogging it and having a specific gravity greater than 1.00.

2. A tablet formulation according to claim 1 wherein the pesticide is a herbicide.

3. A tablet formulation according to claim 1 wherein the pesticide is a fungicide.

4. A tablet formulation according to claim 1 wherein the pesticide is an insecticide.

5. A tablet formulation according to claim 1 wherein the pesticide is a nematocide.

6. A tablet formulation according to claim 1 wherein the pesticide is an acaricide.

7. A tablet formulation according to claim 1 wherein the pesticide is a bactericide.

8. A tablet formulation according to claim 1 wherein a growth regulant is used.

9. A tablet formulation according to claim 2 wherein the herbicide is 3-cyclohexyl-6-dimethylamino-1-methyl-1,3,5-triazine-2,4(1H, 3H)-dione.

10. A tablet formulation according to claim 2 wherein the herbicide is (2,4-dichlorophenoxy) acetic acid.

11. A tablet formulation according to claim 2 wherein the herbicide is a sulfonamide.

12. A tablet formulation according to claim 11 wherein the sulfonamide is 3-[[[[(4-methoxy-6-methyl-1,3,5-triazin-2-yl)amino]carbonyl]amino]sulfonyl]-2-thiophene carboxylic acid, methyl ester.

13. A tablet formulation according to claim 11 wherein the sulfonamide is methyl 2-[[[[(4-methoxy-6-methyl-1,3,5-triazin-2-yl)-amino]carbonyl]amino]sulfonyl]benzoate.

14. A tablet formulation according to claim 11 wherein the sulfonamide is ethyl 2-[[[[(4-chloro-6-methoxy-2-pyrimidinyl)amino]carbonyl]amino]sulfonyl]benzoate.

15. A tablet formulation according to claim 12 comprising 52% of said sulfonamide, 10% of citric acid, 26% of sodium bicarbonate, 5% of a condensate of naphthalene sulfonic acid salt and ammonium salt, 1% of cross-linked polyvinylpyrrolidone, 1% of sodium dialkyl sulfosuccinates, and 5% of boric acid.

16. A tablet formulation according to claim 15 comprising 52.1% of said sulfonamide, 25.6% of sodium bicarbonate and 0.3% of magnesium stearate.

17. A tablet formulation according to claim 3 wherein the fungicide is methyl-2-benimidazole carbamate.

18. A tablet formulation according to claim 4 wherein the insecticide is trans-5-(4-chlorophenyl)-N-cyclohexyl-4-methyl-2-oxothiazolidine-3-carboxamide.

19. A tablet formulation according to claim 6 wherein the acaricide is (4RS, 5RS)-5-(4-chlorophenyl)-N-cyclohexyl-4-methyl-2-oxo-1,3-thiazolidine-3-carboxamide.

20. A tablet formulation according to any one of claims 1 to 19 in the form of a tablet.

* * * * *